US010109172B1

(12) United States Patent
Werner et al.

(10) Patent No.: US 10,109,172 B1
(45) Date of Patent: *Oct. 23, 2018

(54) NOISE LEVEL TRACKING AND NOTIFICATION SYSTEM

(71) Applicant: International Business Machines Corporation, Armonk, NY (US)

(72) Inventors: John S. Werner, Fishkill, NY (US); Arkadiy O. Tsfasman, Wappingers Falls, NY (US); Byron S. Green, Poughkeepsie, NY (US); William L. Brodsky, Binghamton, NY (US); Jeffrey A. Newcomer, Poughkeepsie, NY (US); Robert K. Mullady, Highland, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/855,250

(22) Filed: Dec. 27, 2017

Related U.S. Application Data

(63) Continuation of application No. 15/489,943, filed on Apr. 18, 2017.

(51) Int. Cl.
| | | |
|---|---|---|
| *G08B 21/02* | (2006.01) | |
| *H04R 29/00* | (2006.01) | |
| *G08B 21/18* | (2006.01) | |

(52) U.S. Cl.
CPC ............ *G08B 21/02* (2013.01); *G08B 21/182* (2013.01); *H04R 29/00* (2013.01)

(58) Field of Classification Search
CPC ....... G08B 21/02; G08B 21/182; H04R 29/00
See application file for complete search history.

(56) References Cited

U.S. PATENT DOCUMENTS

| | | |
|---|---|---|
| 3,729,598 A | 4/1973 | Tegt et al. |
| 5,317,273 A | 5/1994 | Hanson et al. |
| 6,456,199 B1 | 9/2002 | Michael |
| 6,831,984 B2 | 12/2004 | Sapiejewski |
| 7,574,917 B2 | 8/2009 | Von Dach et al. |
| 8,170,228 B2 | 5/2012 | Goldstein et al. |
| 8,391,503 B2 | 3/2013 | Bayley et al. |
| 2008/0015463 A1 | 1/2008 | Goldstein |
| 2008/0144842 A1 | 6/2008 | Goldstein et al. |
| 2009/0080670 A1 | 3/2009 | Solbeck et al. |
| 2010/0135502 A1 | 6/2010 | Keady et al. |
| 2012/0321094 A1 | 12/2012 | Schiller et al. |
| 2013/0094658 A1 | 4/2013 | Holter |

(Continued)

FOREIGN PATENT DOCUMENTS

WO     2005/125270 A1     12/2005

OTHER PUBLICATIONS

Berger, E., "Preferred Methods for Measuring Hearing Protector Attenuation," RIO Inter Noise 2005: The 2005 Congress and Exposition on Noise Control Engineering, Aug. 2005, 10 pages.

(Continued)

*Primary Examiner* — David Ton
(74) *Attorney, Agent, or Firm* — Jay Wahlquist

(57) ABSTRACT

A first value is received and is associated with a noise level of an environment that a user is in. It is determined whether the first value exceeds a first threshold. A second computing device is notified when the first value exceeds the first threshold. The notifying indicates that the user must leave the environment.

7 Claims, 8 Drawing Sheets

(56) References Cited

U.S. PATENT DOCUMENTS

| | | |
|---|---|---|
| 2014/0247952 A1 | 9/2014 | Goldstein |
| 2014/0294191 A1 | 10/2014 | Parkins |
| 2015/0055784 A1 | 2/2015 | Brayton |
| 2016/0374595 A1 | 12/2016 | Henriksen et al. |

OTHER PUBLICATIONS

Werner et al., "Noise Level Tracking and Notification System," U.S. Appl. No. 15/489,943, filed Apr. 18, 2017.

List of IBM Patents or Patent Applications Treated as Related, Signed Dec. 27, 2017, 2 pages.

NOISE LEVEL TRACKING AND NOTIFICATION SYSTEM

BACKGROUND

This disclosure relates generally to hearing protection devices, and more specifically to tracking noise levels and sending notifications accordingly.

For a given job plan, a worker such as a technician, equipment engineer, or production worker may be required or encouraged to adhere to hearing protection protocols (e.g., Occupational Safety and Health Administration (OSHA) safety standards). Users that do not follow these protocols may experience various forms of ear damage such as noise induced hearing loss (NIHL). In an illustrative example of specific protocols, OSHA requires hearing protection in an environment that has noise levels at or above 85 decibels (dB). At 95 dBs or greater, a user may experience ear damage after 4 hours of exposure per day. At 100 dBs or greater, a user may experience damage after only 2 hours per day. And at 120 dB or greater, a user may experience damage almost immediately.

Maintaining functional hearing after exposure to these environments can be difficult for various reasons. For example, users may not realize that the environment is above a hazardous noise level. Users may also not realize that a seemingly nonhazardous noise level will become hazardous after a particular quantity of time. Further, users may not have hearing protection available. Users may also forget to place hearing protection back on after an extended break or may even be wearing hearing protection incorrectly. In some situations, hearing protection devices may be inadequately attenuating or defective without the user knowing it.

SUMMARY

One or more embodiments are directed to a computer-implemented method, a hearing protection device and a system. A first computing device may receive a first value from a hearing protection device. The first value may be associated with a noise level of an environment that a user is in. The first computing device may determine that the first value exceeds a first threshold. In response to the determining that the first value exceeds the first threshold, a second computing device may be notified. The notifying may indicate that the user must leave the environment within a particular time interval.

Figure 1:
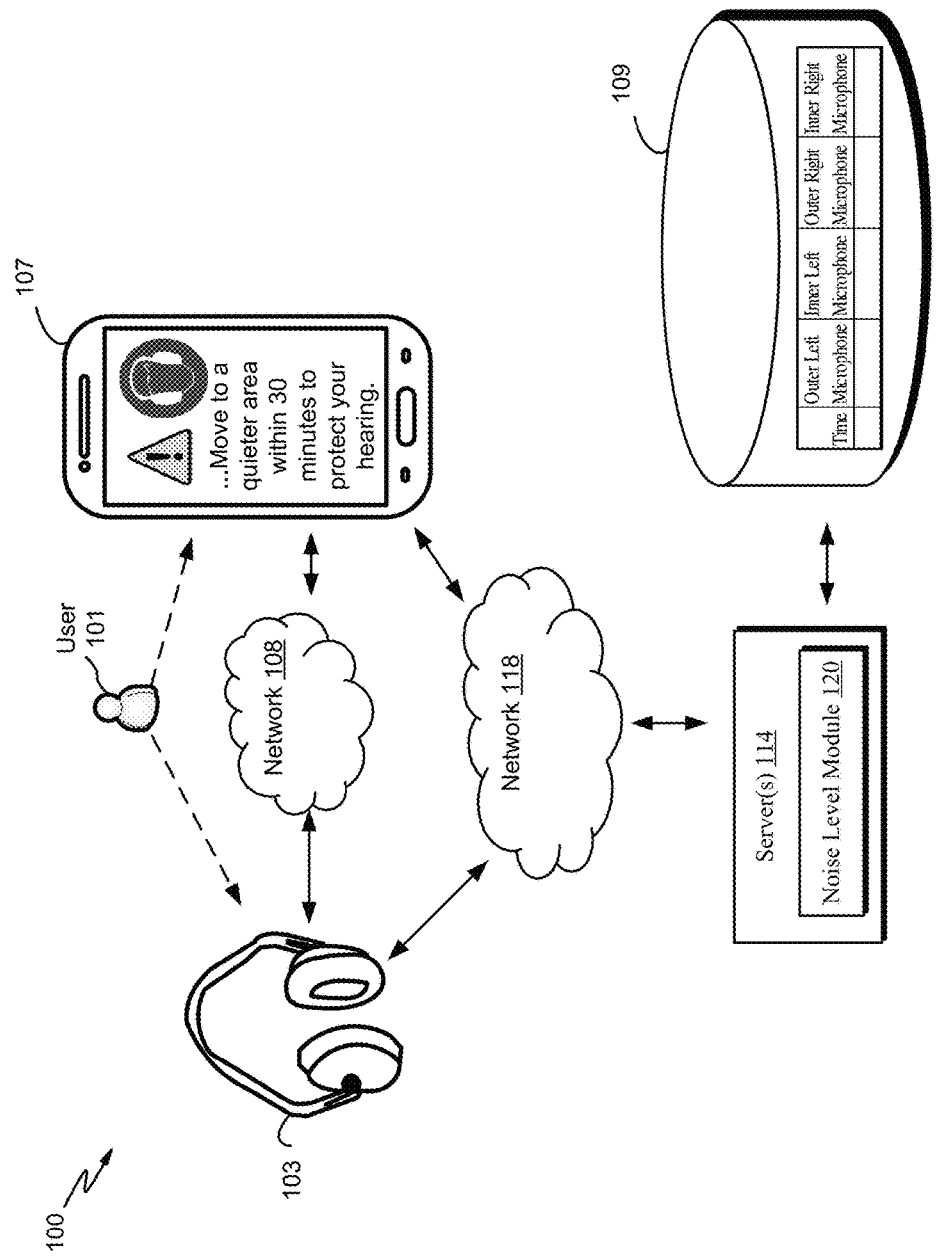
FIG. 1 is a block diagram of a computing environment, according to embodiments.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

Aspects of the present disclosure relate to tracking noise levels and sending notifications accordingly. While the present disclosure is not necessarily limited to such applications, various aspects of the disclosure may be appreciated through a discussion of various examples using this context.

Current hearing protection device technologies may inadequately address the difficulty of maintaining healthy hearing after exposure to noisy environments. Some of the current technologies involve improving the wearing comfort of a user and improving the ear protection device mediums for increased noise filtering (e.g., silicon-based ear plugs). However, even with these technologies, users may still experience ear structure damage for the reasons stated above. Accordingly, some embodiments of the present disclosure address some or each of these problems and improve hearing protection device technology as described below.

FIG. 1 is a block diagram of a computing environment 100, according to embodiments. The computing environment 100 includes the user device 107 and hearing protection device 103, each of which are communicatively coupled (e.g., via the network 108 and/or 118) with each other and to the server(s) 114. In some embodiments, the computing environment 100 is implemented within a cloud computing environment, or use one or more cloud computing services. Consistent with various embodiments, a cloud computing environment includes a network-based, distributed data processing system that provides one or more cloud computing services. Further, a cloud computing environment may include many computers, hundreds or thousands of them or more, disposed within one or more data centers and configured to share resources over the network 118. For example, the server(s) 114 may be part of a cloud computing system.

Figure 8:
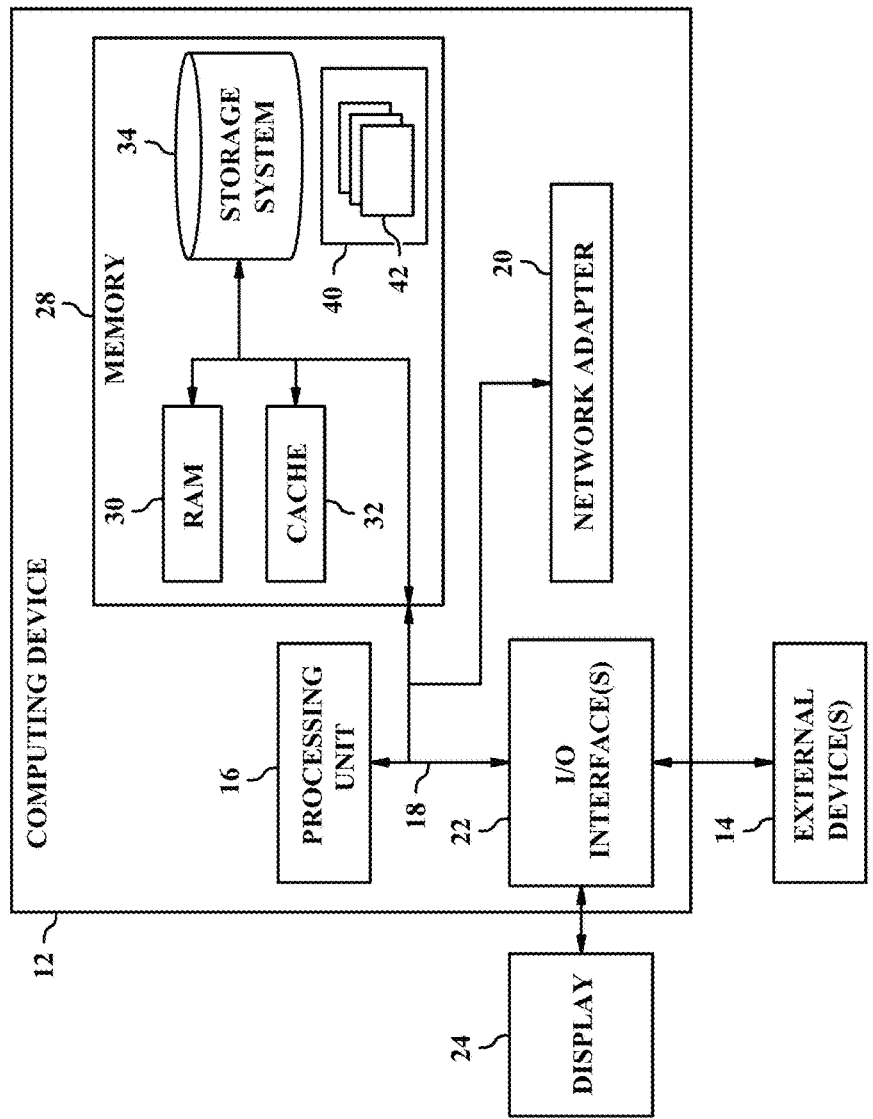
FIG. 8 is a block diagram of a computing device, according to embodiments.

Consistent with some embodiments, the user device 107 and/or the server(s) 114 are configured the same as or analogous to the computing device 12 as illustrated in FIG. 8. In some computing environments, more or fewer components may be present than illustrated in FIG. 1. For example, the server(s) 114 may transmit notifications to additional user devices. In another example, only one of the networks (e.g., network 118) are present.

The user device 107 and/or hearing protection device 103 establishes a connection or communicate with the server(s) 114 via the network 118, which may be any suitable network such as a local area network (LAN), a general wide area network (WAN), and/or a public network (e.g., the internet). Likewise, the user device 107 and the hearing protection device 103 may communicate with each other via the network 108. The network 108 may also be any suitable network, such as a personal area network (PAN) (e.g., Bluetooth®, as developed by Bluetooth Special Interest Group (SIG)).

The user 101 has access to at least user device 107 and hearing protection device 103. The user device 107 may be any device, such as a mobile phone, a laptop computing device, a tablet, a smart watch, or any other suitable device, such as those described in FIG. 8. The hearing protection device 103 may also be any suitable hearing protection device capable of protecting one or more ear structures and/or preserve functions of one or more ears, such as hearing. For example, the hearing protection device 103 may be ear muffs, as illustrated in FIG. 1. In some embodiments, the hearing protection device is one or more ear plugs that are configured to be inserted at least partially into one or more ear canals to preserve user hearing and protect physical structures in the inner ear, such as the cochlea. As described in more detail below, the hearing protection device 103 may be equipped with one or more transmitters to transfer noise level data to the user device 107 and/or the server(s) 114.

The server(s) 114 may be one or more computing devices that execute requests from the user device 107 and/or the hearing protection device 103 over the network 118. The noise level module 120 populates data in the data store 109 and performs various functions and calculations, as described in more detail below. In some embodiments, the user device 107 and/or the hearing protection device 103 includes the noise level module 120 in addition to or instead of the server(s) 114. In some embodiments, the data store 109 includes a history of values, which are associated with the same or different hearing protection devices or computing devices at different points in time. For example, in a working environment, the data store 109 may include microphone or noise level readings of a plurality of worker hearing protection devices at particular intervals (e.g., every 1 minute).

FIG. 1 illustrates at least that the hearing protection device 103 measures and identifies noise levels of an environment that the user 101 is in and data is analyzed, compared, calculated, stored, and notifications are sent accordingly. For example, the hearing protection device 103 measures or obtains (e.g., via a microphone) a particular noise level that the environment is experiencing. The hearing protection device 103 may then transmit converted digital data corresponding to the particular noise level to the server(s) 114 and/or the user device 107. The time or timestamp of when the data was measured, transmitted, and/or received may be input into the data store 109 and/or the user device 107. Noise level measurement values may also be populated in the data store 109 and/or user device 107 as illustrated. The noise level module 120 may then analyze and compare the measurement and timestamp values to a set of criteria (e.g., Occupational Health and Safety Standards (OH&S), OSHA, etc.), as described in more detail below. And based on whether the criteria is met, in some embodiments, the server(s) 114 transmits a notification to the user device 107. For example, the notification may include the indicia specified on the user device 107 that based on the noise level, the user 101 should move to a quieter areas within 30 minutes to protect his or her hearing. In some embodiments, the server(s) 114 may in addition or instead transmit the notification to the hearing protection device. For example, such notification may come in the form of an auditory warning, Light Emitting Diode (LED) warning, etc.

In some embodiments, upon one or more thresholds being met, the server(s) 114, the user device 107, and/or the hearing protection device 103 may transmit a message to equipment that the user 101 is working with, which may cause a shutdown of the equipment such that a noise level will fall below a threshold. For example, if the user 101 is working with a drill that causes the dB level to exceed a threshold, the server(s) 114 may transmit a message to a receiver attached to the drill, and the drill may include logic that shuts itself down in response to the receiving of the message. This may protect the user 101's hearing.

Figure 2:
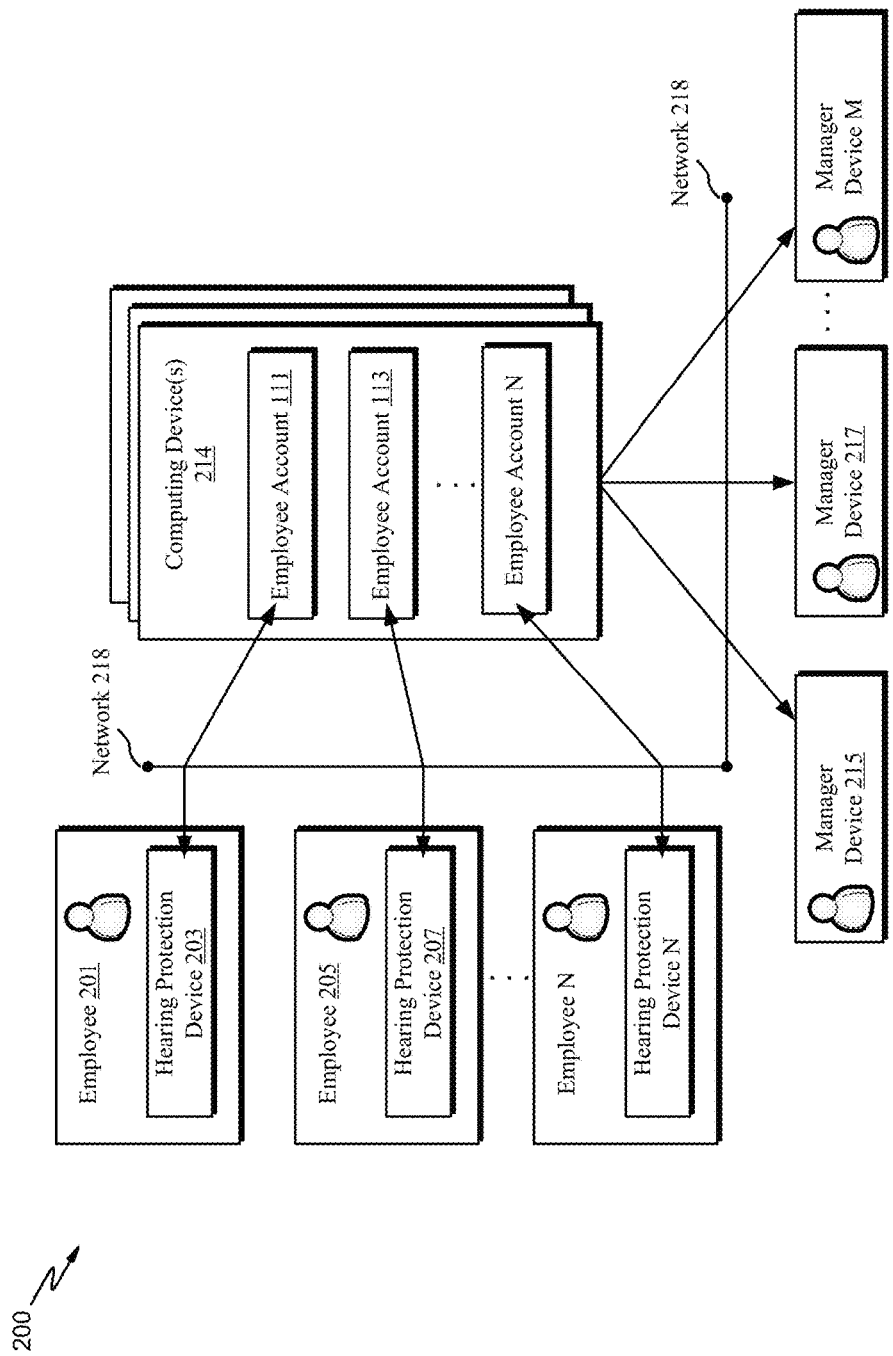
FIG. 2 is a block diagram of a computing environment, according to embodiments.

FIG. 2 is a block diagram of a computing environment 200, according to embodiments. FIG. 2 illustrates that the computing environment 200 may be associated with a company or job environment where hearing protection is required or encouraged. FIG. 2 also illustrates that user devices (e.g., the user device 107 of FIG. 1) of employees are not necessary in particular embodiments. For example, the employee 201 may be wearing (or supposed to be wearing) the hearing protection device 203, the employee 205 may be wearing the hearing protection device 207, and various other employees ("N" employee) may also be wearing or are supposed to wear hearing protection devices.

In some embodiments, the computing device(s) 214 represents the server(s) 114 of FIG. 1, which includes the data store 109. The computing device(s) 214 may be a private cloud with a particular company's employee accounts held on the company's backend server. In some embodiments, the computing device(s) 214 represent the user device 107 of FIG. 1. The computing device(s) 214 includes employee accounts 111, 113, and various other employee accounts (employee account N) corresponding to the employee or hearing protection device. These hearing protection devices may measure noise level data and then directly transmit, via the network 218, the data to the computing device(s) 214 and in particular into the employees' respective accounts. These accounts may include employee ID information and information analogous to the information contained in the data store 109 of FIG. 1. Based on the information received and when compared to a set of rules (e.g., OSHA standards), the computing device(s) 214 may then transmit notifications to both the hearing protection devices (e.g., via a visual indicator or speaker on the hearing protection devices) and various manager devices, such as manager device 215 and manager device 217, and/or various other manager devices (manager device M). These manager devices may be user devices of particular managers, bosses corporate health services, and/or other supervisory users that are responsible for or over the employees 205 and 201. Accordingly, specific permissions can be granted to these managers in order to oversee or track whether an employee is wearing appropriate hearing protection and is adhering to safety protocols. For example, each manager may be sent the notification specified on the user device 107 of FIG. 1.

Figure 3:
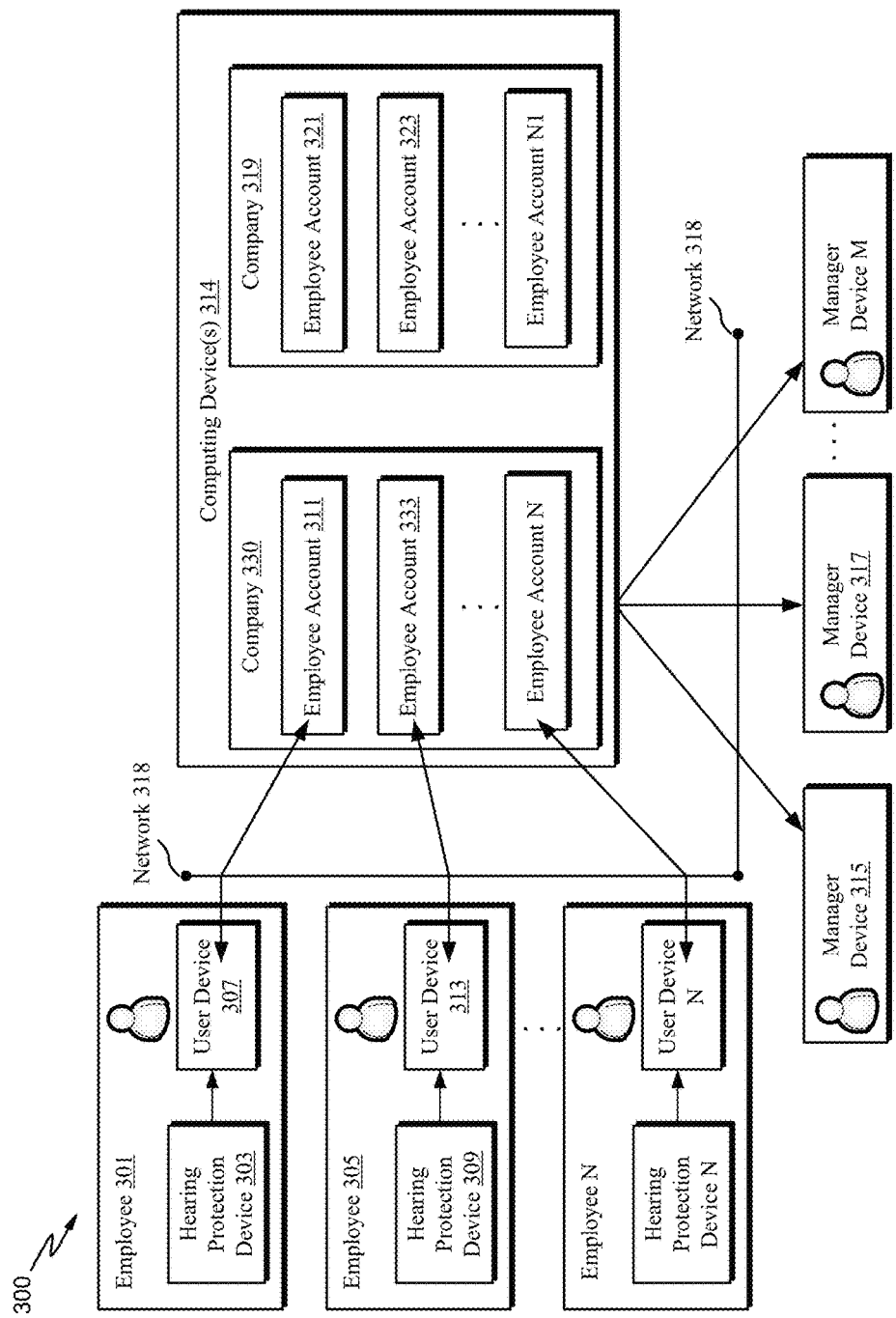
FIG. 3 is a block diagram of a computing environment, according to embodiments.

FIG. 3 is a block diagram of a computing environment 300, according to embodiments. FIG. 3 illustrates that embodiments may incorporate user devices of employees within the context of a company or work environment. The employee 301, for example, may have a user device 307, such as a mobile phone. The employee 301 may also be wearing the hearing protection device 303. The hearing protection device 303 may measure a noise level of the environment that the employee 301 is in. This data may then be transmitted to the user device 307 (e.g., via a Bluetooth® network). The user device 307 may then transmit the same data, via the network 318, to the computing device(s) 314, and the data may be populated in the employee 301's account, which is employee account 311. The same actions may be performed for employee 305 and each worker that is a part of company 330. Other company accounts may also be located on the computing device(s) 314, such as company 319. As illustrated in FIG. 3, for company 330, notifications may be transmitted to the manager devices 315, 317, and/or any other manager device (manager device M). In some embodiments, the computing environment performs all or some of the functions and includes the same components associated with the FIG. 1 and/or FIG. 2 computing environments.

Figure 4:
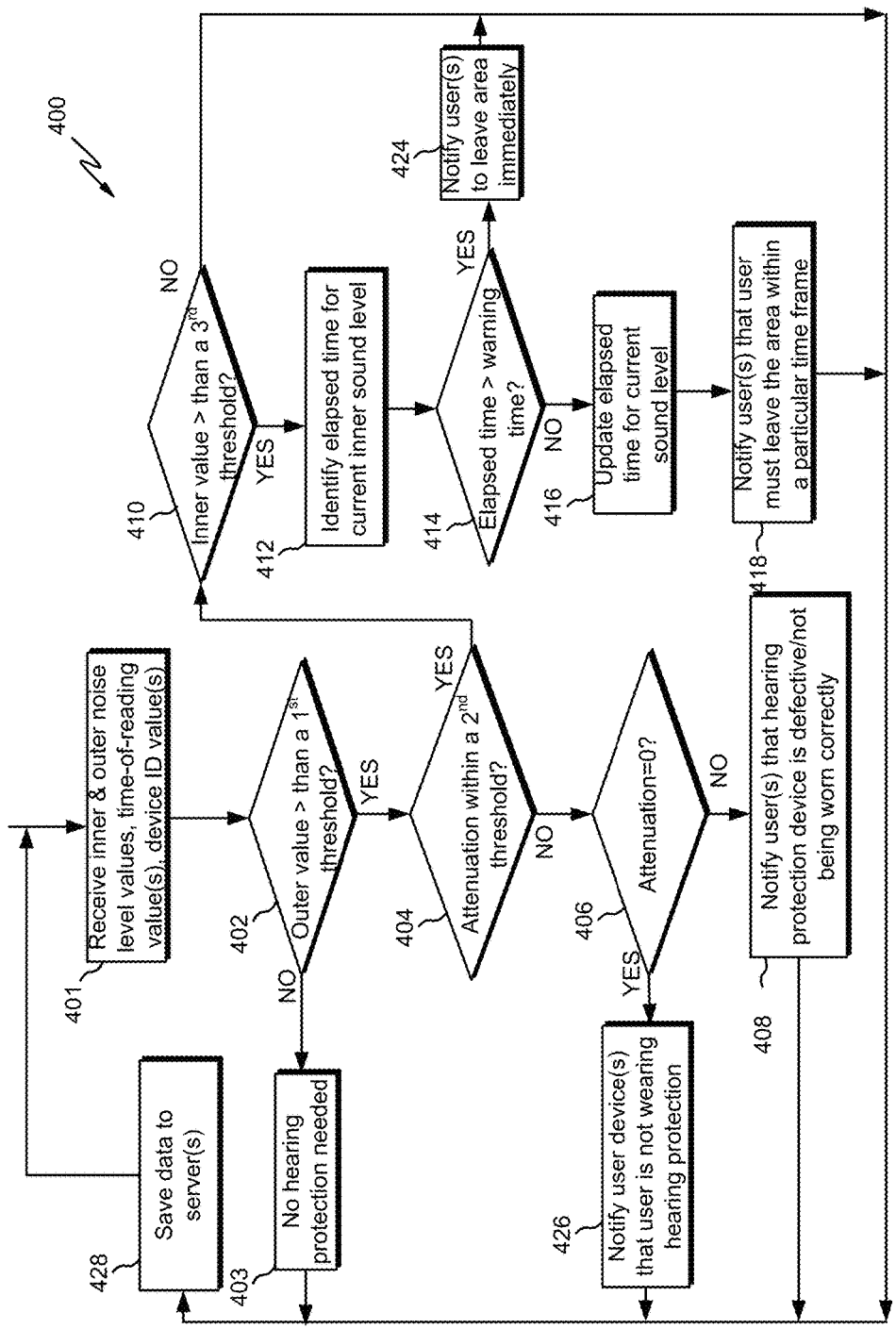
FIG. 4 is a flow diagram of an example process for analyzing noise level data and sending appropriate notifications, according to embodiments.

FIG. 4 is a flow diagram of an example process 400 for analyzing noise level data and sending appropriate notifications, according to embodiments. The process 400 begins at block 401 when inner and outer noise level values, time-of-reading values, and ID values are received. In some embodiments, only some of these values at block 401 are received. In an illustrative example, the hearing protection device 103 of FIG. 1 may include a microphone(s) at the inside of the hearing protection device that picks up the inner sound level values, which may be converted by an analog-to-digital converter and transmitted to a server computing device that performs block 401. The inside of the hearing protection device may be the inner portion that is oriented toward the ear of a user. Likewise another microphone(s) on the outside of the hearing protection device may measure the outer sound levels and transmit them to a server computing device. The outer portion of the hearing protection device faces away from the user toward the environment he/she is in. The ID values may correspond to a hearing protection device ID (e.g., a device fingerprint, IP address) such that the particular user or hearing protection device may be identified for notification or communication purposes. Time-of-reading values may be a time or timestamp that the noise level values are measured, transmitted, and/or received. In some embodiments, some or all of the process 400 is performed by the hearing protection device itself and/or a user device and not a server computing device.

Per block 402, it may be determined (e.g., by the noise level module 120 of FIG. 1) whether the outer noise value is greater than a first threshold. In some embodiments, the first threshold (and/or any threshold as described herein) corresponds to one or more policies/rules or particular noise level avoidance criteria and/or other ear/hearing protection criteria. For example, the policies may be included in a data structure (e.g., the data store 109 of FIG. 1) that specifies each of the OSHA standards for avoiding noisy environments according to the table below:

TABLE 1

| dB Level | When Hearing Damage Occurs |
|---|---|
| <85 | No damage |
| 95 | After 4 hours of exposure per day |
| 100 | After 2 hours of exposure per day |
| 105 | After 1 hour of exposure per day |
| 110 | After 30 minutes of exposure per day |
| 115 | After 15 minutes of exposure per day |
| 120 | Immediately |

In an illustrative example, the first threshold may be 85 dB. Accordingly, per block 403, if the outer noise level value is not greater than the first threshold (85 dBs), then no hearing protection is needed. Information indicating that no hearing protection was needed for a particular user at the particular noise level readings and timestamp may then be saved to one or more servers (e.g., the server(s) 114 of FIG. 1), per block 428.

Per block 404, if it is determined that the outer noise value is greater than the first threshold, it may be determined (e.g., by the noise level module 120 of FIG. 1) whether the attenuation difference of the inner and outer noise level values are within a second threshold. When noise or sound travels through a medium (e.g., ear muffs), its intensity diminishes with distance. Noise intensity diminishes because of scattering and absorption. Scattering is the reflection of the sound in directions other than its original direction of propagation. Absorption is the conversion of the sound energy to other forms of energy. The quantity of absorption may depend on the medium type and/or mass and density of hearing protection. The combined effect of scattering and absorption is attenuation. For calculation purposes, the attenuation may be a quantity of noise level reduction (i.e., the difference or delta) between the outer noise level to the inner noise level. Hearing protection devices with higher attenuation (i.e., a greater difference between outer noise levels and inner noise levels) reduce more noise.

The second threshold at block 404 may correspond to the quantity or range of attenuation that should occur according to the particular hearing protection device being worn. At least some hearing protection devices are supposed to attenuate or reduce the noise level at a particular value. For example, a hearing device manufacture may specify that its hearing protection device should have an attenuation value of 16 dB and this value may be stored (e.g., to the data store 109 of FIG. 1). Accordingly, at block 404 the attenuation difference may be "within" the second threshold if the attenuation is between 14-18 dBs. In some embodiments, the second threshold may correspond to a single data point instead of a range. For example, at block 404 it may be determined whether the attenuation exceeds 15 dBs. If it does, block 410 may be performed. If it does not, block 406 may be performed.

Per block 406, if the attenuation is not within the second threshold (or does not exceed the second threshold), it may be determined (e.g., by the server(s) 114) whether the attenuation is a value of zero or substantially close to zero (e.g., 0.4, 0.8, 1.0, etc.). Per block 426, if the attenuation difference is zero or substantially close to zero user device(s) may be notified (e.g., by the computing device(s) 107) that a user is not wearing a hearing protection device and should be wearing one. If the attenuation has a value of zero or close to it, this may indicate that the inner and outer microphones at the hearing protection device are picking up sound at the same level and therefore there is no attenuation. For example, if a user placed his/her hearing protection device on the ground because of an extended break and started working again, the worker may forget to place his/her ear protection back on and start working with high noise equipment. Both inner and outer microphones may measure noise levels at 95 dBs because the user has not placed the hearing protection device on his/her ears (i.e., there is no absorption and there is a high quantity of signal scattering). A notification may then be transmitted to the worker's mobile device to remind him/her that he/she is working at a dangerous noise level and that he/she should put on hearing protection because at a level of 95 dBs, hearing loss will occur after 4 hours of exposure.

Per block 408, if the attenuation value is not zero or substantially close to zero, a notification may be sent (e.g., by the server(s) 114) to user(s) that the hearing protection device is defective or not being worn correctly. For example, using the illustration above, if a manufacture indicates that a hearing protection device's attenuation level should be 16 dBs, but is only experiencing 5 dBs, this value of 5 may be outside of the second threshold (14 dB to 18 dB) at block 404 but higher than the value of zero at block 406. This may indicate that there is still attenuation but there is some other problem. For example, the user may have slightly rotated one of the ear muffs such that there is less absorption of some of the sound waves emitted in the environment and therefore less attenuation and potential for hearing damage. In another example, the hearing protection device may have been punctured, absorption material may have been removed, or some other damage to the ear protection device may have resulted that causes a reduction in attenuation levels compared to policy levels.

Per block 428, data may then be saved to servers(s) or some other computing device. For example, the time-of-reading values and inner and outer noise level values at block 402, the attenuation difference at block 404, and/or the type of notifications sent according to blocks 426 and 408 may be recorded and saved to the data store 109 of FIG. 1. Saving data at block 428 is the final step of all functions in FIG. 4 and may be useful for several purposes. For example, administrators may be able to track how noisy working environments are, how well hearing devices are attenuating, and/or how often workers are properly using hearing protection. Supervisory administrators may determine if each worker is adhering to hearing protection protocols on a consistent basis and notify workers when it is problematic.

These data recorded at block 428 may also be very helpful for companies in a litigation setting. For example, if a worker files a civil negligence action against an employer for hearing loss damages, the employer may use this data (1) as an affirmative defense that the worker contributed to any negligence by not wearing or incorrectly wearing his hearing protection device and was repeatedly notified about it; and (2) the employer could have sufficient data to prove that the hearing loss damages that the worker experienced was not caused by the employer working environment. For example, the data store 109 may indicate that the inner dB noise level at the inside of the hearing protection device never exceeded 85 dBs while a particular worker was working, which does not cause hearing damage. Therefore, the employer may prove that the worker's damages were caused by something other than the employer's hearing protection equipment or work environment.

Per block 410, if the attenuation difference is within (or exceeds) the second threshold according to block 404, then it may be determined (e.g., by the noise level module 120) whether the inner noise level value exceeds a third threshold. The inner value may correspond to the noise level that an ear of a user is exposed to for hearing damage purposes. In some embodiments, the third threshold is the same value as the first threshold (e.g., 85 dB). Accordingly, for example, if the inner value is not greater than the third threshold no further action may be taken except to store this data to the server(s) at block 428 because hearing or ear damage is not at stake.

Conversely, at block 412, if the inner noise level value exceeds the third threshold, then an elapsed time may be identified for the current inner sound level/inner value. Therefore, an elapsed time that the user has been exposed to noise levels at or above (or within a threshold of) the inner value may be determined. For example, the process 400 may occur in a looped or polled fashion as illustrated. Accordingly, for example, the time-of-reading values and the noise level for the same user (ID value) at block 401 may have been measured or polled repeatedly for 10 minutes in response to the illustrated conditions in the process 400 being met. For example, at a first time (e.g., the time specified at block 401) the inner value may have exceeded the third threshold. The hearing protection device may have taken another noise level sample at a second time (e.g., 1 minute later) and at block 402 the elapsed time would therefore be identified by taking the difference between the first time stamp and the second time stamp.

Per block 414, it is determined (e.g., by the noise level module 120) whether the elapsed time exceeds the warning time by comparing the two times. In some embodiments, the warning time is a critical time according to particular stored polices. Accordingly, the warning time may include one or more policies specifying how long a user should be exposed to particular noise level(s) before hearing damage occurs. For example, referring back to table 1, the warning time may be one or more of the listed times under the "When Hearing Damage Occurs" column. In some embodiments, the warning time is some other predetermined time, such as time periods before the critical time periods listed in table 1.

At block 424, if the elapsed time exceeds the warning time, a notification may be sent to one or more users/devices that the user exposed to the inner value above the third threshold should leave the area immediately. This is because ear or hearing damage may result after a particular quantity of time at a particular noise level. This data may then be saved to the server(s) at block 428.

Per block 416, if the elapsed time does not exceed the warning time at block 414, the elapsed time may be updated for the current sound level represented by the inner value. Per block 418, user(s)/user devices may be notified that the user exposed to the inner value must leave the area within a particular time interval. For example, at block 416 the elapsed time may have been 10 minutes since the first reading at a particular inner noise level. Accordingly, a user device (e.g., the user device 107 of FIG. 1) may be notified to prompt the associated user to leave the area within 20 minutes based on what the warning time value is, such as 30 minutes. This information may then be stored to the server(s) at block 428. The notification at block 418 may thus provide important information to the user regarding the time the user has to finish his/her current task and move to a quieter area.

Figure 5:
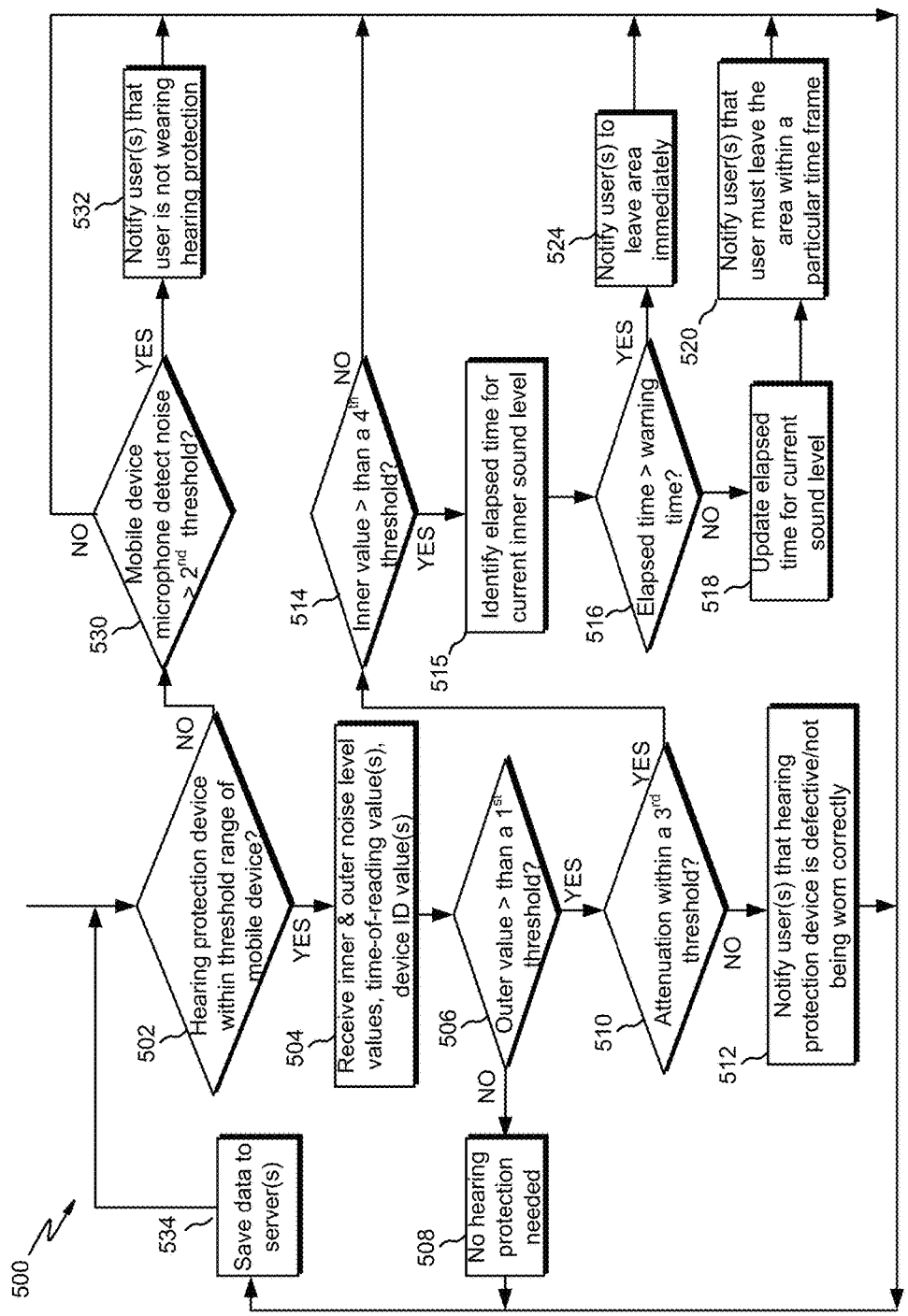
FIG. 5 is a flow diagram of an example process for analyzing noise level data and sending appropriate notifications, according to embodiments.

FIG. 5 is a flow diagram of an example process 500 for analyzing noise level data and sending appropriate notifications, according to embodiments. The process 500 may begin at block 502 when it is determined whether a hearing protection device is within a threshold signal strength range of a user mobile device. The determining at block 502 may be performed to make an inference of whether a user is wearing hearing protection. Block 502 may also be performed to verify that a user does not keep their hearing protection device too far away from their mobile device. If the signal strength between the hearing protection device and the mobile device is below (or outside of) the threshold range, then an inference may be made that the mobile device is at a relatively far distance from the hearing protection device, thereby indicating that the person has removed or is not in possession of the hearing protection device. In various embodiments, the signal strength value at block 502 is any value, such as a value below −70, −80, or −90 decibels (db) in a received signal strength (RSSI) range. The signal strength may alternatively be measured in decibel-milliwatts (dbm), or any other appropriate unit measurement. Moreover, any suitable standards other than RSSI may be utilized, such as received channel power indicator (RCPI). Each threshold signal strength value may correspond to a distance at which a mobile device is from a hearing protection device, such 3 feet, 5 feet, 10 feet or any corresponding value. In some embodiments, the process 500 is the same as process 400 of FIG. 4, except for blocks 502 and 530.

Per block 530, if the hearing protection device is not within a threshold range of the mobile device then the mobile device may determine (e.g., by measuring the noise level via a microphone located on the device) whether the noise level of the environment exceeds a second threshold. If the mobile device determines that the noise level does not exceed the threshold, then this data is transmitted and saved to the server(s) per block 534.

Per block 532, if the mobile device measures a noise level that exceeds the second threshold (e.g., 85 dBs), then user(s)/user devices may be notified that the user is not wearing hearing protection and because the second threshold has been exceeded, the user must wear hearing protection. This data may then be transmitted and saved to the server(s) per block 534.

Per block 504, if it is determined that the hearing protection device is within a threshold range of the mobile device, then inner and outer noise level value(s), time stamp value(s), and/or device ID value(s) may be received (e.g., by the hearing protection device 103 of FIG. 1). Per block 506, it may be determined (e.g., by the hearing protection device 103) whether the outer noise level value exceeds the first threshold. If it does not, then no hearing protection is needed by block 508 and data indicated by block 508 (and other data indicated by blocks 504 and/or 506) may be saved to the server(s) per block 534.

Per block 510, if the outer noise level value exceeds the first threshold it may be determined (e.g., by the hearing protection device 103) whether the attenuation is within or exceeds a third threshold. At block 512, if the attenuation is not within the third threshold (which may be the same value as other thresholds), then a notification may be sent to user(s) that the hearing protection device is defective or not being worn correctly by a particular user. This data, including the device ID of the user, the attenuation readings, the inner and outer values, and/or time stamp values may then be saved to the server(s) at block 534.

Per block 514, if the attenuation is within (or exceeds) the third threshold, it may be determined whether the inner noise level value exceeds a fourth threshold. In embodiments, the first threshold, the second threshold, and the fourth threshold are all the same value (e.g., 85 dBs). If the inner value does not exceed the fourth threshold, this means that the user wearing the hearing protection device will not experience ear damage. This information may then be saved to the server(s) per block 534.

Per block 515, if the inner value does exceed the fourth threshold then an elapsed time may be identified (e.g., by the hearing protection device 103) for the current inner noise level that corresponds to the inner noise level value. At block 516 it may then be determined whether the elapsed time is greater than the warning time. If the elapsed time is greater than the warning time then, per block 524, user(s)/user devices may then be notified to leave the area immediately, as hearing damage will immediately result. This information may then be saved to the server(s) per block 534.

Per block 518, if the elapsed time has not exceeded the warning time, then the elapsed time may be stored in memory and updated for the current noise level or noise level range. Per block 520, in response to the update, one or more users may be notified that the user exposed to the high noise levels must leave the area within a particular time interval. This information may then be saved to the server(s) at block 534.

Figure 6:
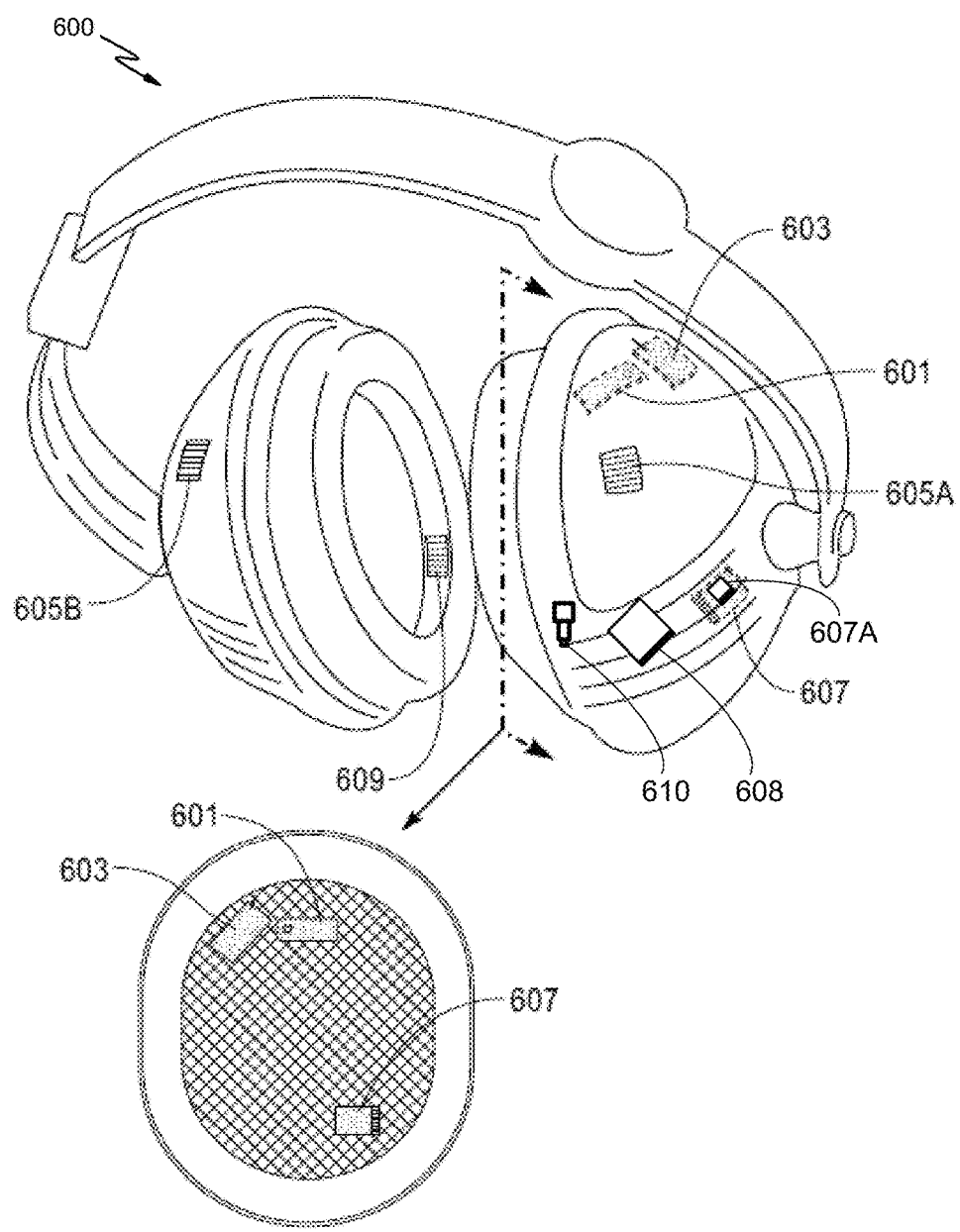
FIG. 6 is a schematic diagram of a hearing protection device, according to embodiments.

FIG. 6 is a schematic diagram of a hearing protection device 600, according to embodiments. In some embodiments, the hearing protection device 600 represents the hearing protection device 103 of FIG. 1 and vice versa. The hearing protection device 600 includes built-in outer microphones 605A and 605B, built-in inner microphone(s) 609, a first transmitter 601 (e.g., a Bluetooth® transmitter), a second transmitter 603 (e.g., a Wi-fi (IEEE 802.11) transmitter), a storage device 607 (e.g., a RAM chip, Secure Digital (SD) card, flash device, etc.), which may include one or more program modules 607A.

The outer microphones 605A and 605B are configured to measure the noise level of the environment that a user is in. (e.g., the outer values at block 401 of FIG. 4). The inner microphone(s) 609 are configured to measure the noise level at an immediate area surrounding the inside of the ear muffs 600 (e.g., the inner values at block 401 of FIG. 4). For example, if the user is wearing the ear muffs, the inner microphone(s) 609 may measure the noise level between the outer portion of a user ear and the inside of the ear muff that is disposed over the ear. In some embodiments, the outer microphones 605A and 605B and/or the inner microphone(s) 609 records frequencies/amplitudes by varying the sampling rate—i.e., the duration at which noise levels are measured and stored. Accordingly, full sound waves for a continuous or extended duration may not be recorded. One potential advantage of this is that it allows for more privacy. In an illustrative example, measuring the noise level every 10 seconds may preserve privacy of individuals who are having private conversations because the entire conversation is not recorded.

The first transmitter 601 and the second transmitter 603 are utilized to transmit various sets of data over one or more networks. In some embodiments, the hearing protection device 600 includes a processor(s) 608, such as a microcontroller, a signal conditioning component (not shown) and/or a pressure transducer 610, which can include an analog-to-digital converter (not shown). These components together may filter, amplify, and convert analog noise level signals picked up from the microphones to digital signals so that digital data can be analyzed and/or transmitted over one or more networks. The first transmitter 601 is configured to transmit data using minimal power consumption to a secondary device. For example, the first transmitter may be a Bluetooth® transmitter that transmits data over a personal area network (e.g., the network 108 of FIG. 1) to a user's mobile device. The second transmitter 603 may be configured to transmit data over a different type of network (e.g., the network 118 of FIG. 1), such as to a backend server. In some embodiments, there is no conversion of the analog signals to digital signals. Accordingly, analog signals may be transmitted to another device where data is then converted to digital data and analyzed. In some embodiments, the hearing protection device 600 only has either the first transmitter 601 or the second transmitter 603 (or one transmitter is inactivated) but not both.

The storage device 607 may include various sets of data and program instructions (program module(s) 607A) to be executed by a processor. For example, the storage device 607 may include a switching module. The switching module may be a set of program instructions that, when executed by a processor, determines when and if a communication failure occurs between the hearing protection device 600 and a computing device (e.g., the user device 107 and/or the server(s) 114 of FIG. 1). A "communication failure" may occur when a communication session between devices cannot be initiated and/or maintained. For example, referring back to FIG. 1, a TCP/IP communication session may be requested between the hearing protection device 103 and the server(s) 114 but may fail because of a wrong server address, the server(s) 114 is down or disabled, and/or a firewall may block communications to a particular port. In another example, a user's mobile device may be outside of a signal strength threshold range of the hearing protection device 600 or the mobile device battery may be dead such that a communication session cannot be established.

The switching module may be configured to determine or receive information indicating that a communication session cannot be established. In response to the determining or receiving of this information and analyzing data, the switching module may populate data within the storage device 607 to store noise level information gathered from the microphones (or any other information). For example, such information may include data populated in the data store 109 of FIG. 1 and/or the data stored to the server(s) at blocks 428 and/or 534 of FIG. 4 and FIG. 5 respectively. The switching module may effectively allow for local processing and storing of data in times where other resources are unavailable. In particular embodiments, as a background task, the switching module or other function instructs the hearing protection device 600 to poll or request a communication session after every N period of time after a failure occurs. In this way, data may be uploaded to other resources as soon as communications are established in order to keep heavy computations and data from overloading the storage device 607.

In some embodiments, the program module(s) 607A represent or include a noise level module (e.g., the noise level module 120 of FIG. 1). In some embodiments, the program module(s) represent or include a notification module that may notify, in response to determining that a value exceeds, meets, or is within a threshold, a computing device. For example, the notification module may perform some or all of the notification blocks in FIGS. 4, 5, and/or 7. In some embodiments, the notification module may instead or in addition be located in other computing devices (e.g., the server(s) 114, and/or the user device 107 of FIG. 1). In some embodiments, the program module(s) include or represent some or each of the functions as described in FIGS. 4, 5, and/or 7.

In some embodiments, the hearing protection device 600 includes other components, such as additional sensor(s) for different functions. For example, the hearing protection device 600 may include an accelerometer and/or gyroscope sensor to infer whether or not a user is wearing the hearing protection device 600. In an illustrative example, if a user is wearing the hearing protection device 600, the accelerometer may measure that acceleration of the hearing protection device 600 at some particular value due to, for example, a person wearing the hearing protection device 600 who is walking or initiating some other form of movement. There may be specific policies that indicate that the sensor must maintain a motion threshold for a particular quantity of time and if it does not, a notification may be transmitted (e.g., to the user device 107 of FIG. 1) indicating that the user is not wearing the hearing protection device.

In some embodiments, a pressure sensor may be included in the hearing protection device 600 to infer whether a user is wearing the hearing protection device 600. For example, the pressure sensor(s) may be located at the inferior portion of a headband and/or ear muff(s) such that it measures the level of pressure of a user's head against the hearing protection device 600. If the pressure falls below a threshold, a notification may be transmitted to one or more user devices. In some embodiments, temperature sensors at the inside of the ear muff and outside of the earmuffs may be utilized to infer whether the user is wearing the hearing protection device. For example, in most cases the ambient temperature may be warmer on the inside of the hearing protection device when a user is wearing it when compared to the ambient temperature of the environment that the outside temperature sensors may measure. Accordingly, if the temperature readings from both the inside and outer temperature sensors are different above a threshold, this may indicate that a user is wearing the hearing protection device. Conversely, if the temperature is a same value for both sets of temperature sensors or within a threshold range of each other, this may indicate that the user is not wearing the hearing protection device. Accordingly, a notification may be transmitted to a computing device indicating that the user is not wearing a hearing protection device. In yet other embodiments, a camera sensor may be utilized to infer whether user(s) are wearing hearing protection device(s) by utilizing object recognition algorithms to identify and detect whether user(s) are wearing hearing protection device(s).

Figure 7:
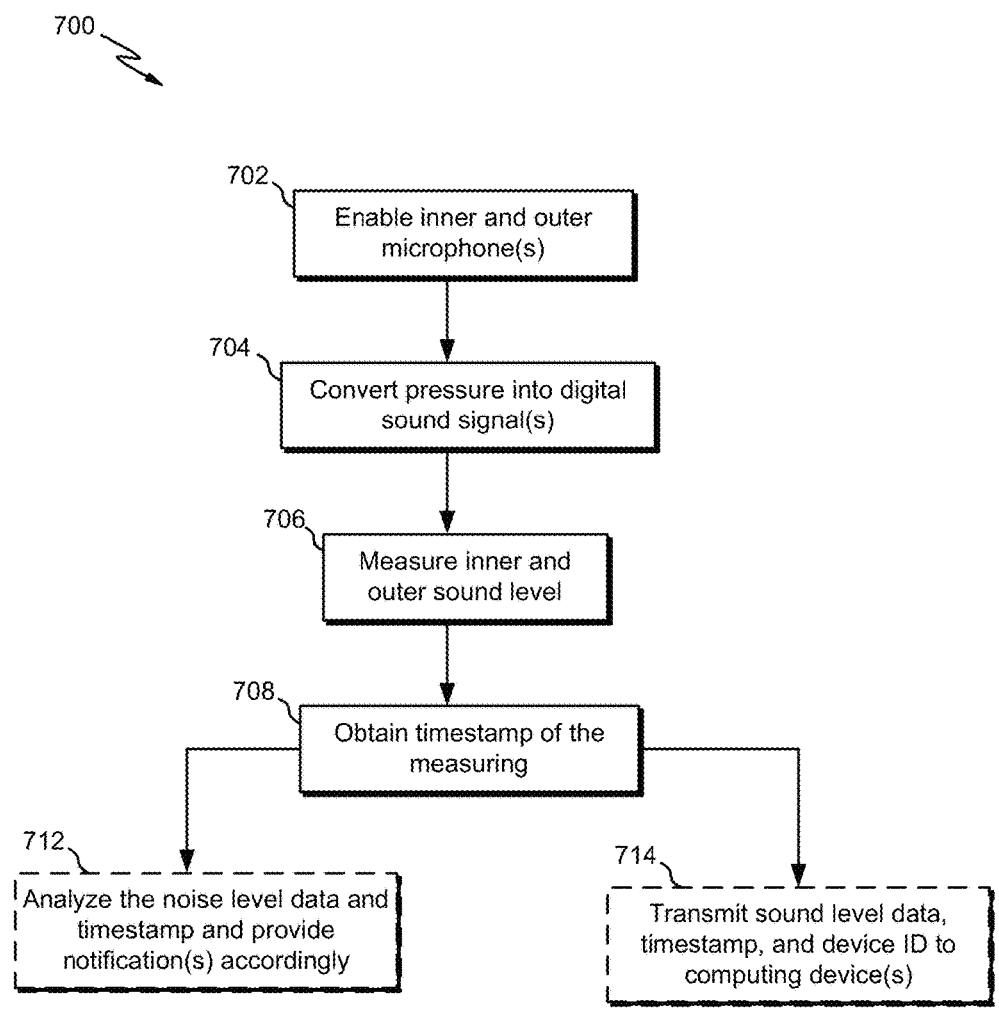
FIG. 7 is a flow diagram of an example process for obtaining data associated with a noise level, according to embodiments.

FIG. 7 is a flow diagram of an example process 700 for obtaining data associated with a noise level at a hearing protection device, according to embodiments. The process 700 may begin at block 702 when the inner and outer microphones are enabled. Enabling may occur via a switch that is user-activated or via a background logic that activates or turns on the hearing protection device every N quantity of time.

Per block 704, pressure may be converted (e.g., via a pressure transducer) to an electrical digital noise signal(s). Sound is defined by pressure variations that a person can detect. Devices may be configured to measure such air pressure and convert them into suitable forms. For example, a pressure transducer may have a sensing element that responds to force applied by fluid pressure. This force deflects a diaphragm, bellows, or Bourdon tube. Such deflections are converted to electrical outputs through any of a variety of different transduction methods.

Per block 706, the inner and outer noise (i.e., sound) levels may be measured. For example referring back to FIG. 6, the microphones 605A, 605B, and 609 may measure the noise levels. At block 708, time stamp value(s) may be obtained or recorded (e.g., via counter logic or timestamp module) indicating when the measuring at block 706 took place.

In some embodiments, per block 714, the noise level data, timestamp, and device ID may be transmitted over a network to one or more computing devices (e.g., the user computing device 107 and/or the server(s) 114). In response to the transmitting, the computing devices may then analyze the data and make corresponding notifications. For example, after the transmission of these data, the computing devices may complete the process 400 and/or 500 of FIG. 4 and FIG. 5 respectively. In some embodiments, per block 712, the hearing protection device itself may analyze the noise level data and timestamp and transmit notifications accordingly. For example, the hearing protection device may include the noise level module 120 of FIG. 1. In another example, the hearing protection device may perform some or part of the process 400 and/or 500 of FIG. 4 and FIG. 5 respectively.

FIG. 8 is a block diagram of a computing device 12, according to embodiments. As shown in FIG. 8, the computing device 12 is shown in the form of a general-purpose computing device, which is not to be construed necessarily by one of ordinary skill in the art as a generic computer that performs generic functions. Rather, the computing device 12 is illustrative only of what components a computing device may include. The components of computing device 12 may include, but are not limited to, one or more processors or processing units 16, a system memory 28, and a bus 18 that couples various system components including system memory 28 to processor 16. In some embodiments, the computing device 12 represents the user device 107 of FIG.

1, the server(s) 114 of FIG. 1, the computing device(s) 214 of FIG. 2, the manager device(s) of FIG. 2, the computing device(s) 309 of FIG. 3, the manager device(s) of FIG. 3, and/or any hearing protection device.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computing device 12 typically includes a variety of computer system readable media. Such media may be any available media that is accessible by computing device 12, and it includes both volatile and non-volatile media, removable and non-removable media.

System memory 28 can include computer system readable media in the form of volatile memory, such as random access memory (RAM) 30 and/or cache memory 32. Computing device 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein. For example, the program modules 42 may be or include the noise level module 120 of FIG. 1 (which may be located in any device) and/or perform any of the portion of the process 400, 500, and/or 700 of FIG. 4, FIG. 5, and FIG. 7 respectively.

Computing device 12 may also communicate with one or more external devices 14 such as a keyboard, a pointing device, a display 24, etc.; one or more devices that enable a user to interact with computing device 12; and/or any devices (e.g., network card, modem, etc.) that enable computing device 12 to communicate with one or more other computing devices. Such communication can occur via Input/Output (I/O) interfaces 22. Still yet, computing device 12 can communicate with one or more networks such as a local area network (LAN), a general wide area network (WAN), and/or a public network (e.g., the Internet) via network adapter 20. As depicted, network adapter 20 communicates with the other components of computing device 12 via bus 18. It should be understood that although not shown, other hardware and/or software components could be used in conjunction with computing device 12. Examples, include, but are not limited to: microcode, device drivers, redundant processing units, external disk drive arrays, RAID systems, tape drives, and data archival storage systems, etc.

Aspects of the present invention may be a system, a method, and/or a computer program product. The computer program product may include a computer readable storage medium (or media) having computer readable program instructions thereon for causing a processor to carry out aspects of the various embodiments.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of embodiments of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of embodiments of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

What is claimed is:

1. A computer-implemented method comprising:
receiving, at a first computing device and from a hearing protection device, a first value, the first value being associated with a noise level of an environment that a user is in;
determining, by the first computing device, that the first value exceeds a first threshold; and
notifying, in response to the determining that the first value exceeds the first threshold, a second computing device, the notifying indicates that the user must leave the environment within a particular time interval;
wherein the first value indicates a first noise level at an inner portion of the hearing protection device.

2. The method of claim 1, the method further comprising:
receiving, from the hearing protection device, a second value, the second value indicates a second noise level at an outer portion of the hearing protection device;
determining that an attenuation between the first and second value is not within a second threshold, the attenuation being an amount of noise level reduction from the first noise level to the second noise level; and
notifying, in response to the determining that an attenuation between the first and second value is not within a second threshold, at least the second computing device, the notifying in response to the determining that an attenuation between the first and second value is not within a second threshold indicates that the user is not wearing the hearing protection device correctly.

3. The method of claim 1, the method further comprising:
receiving, from the hearing protection device, a second value, the second value indicates a second noise level at an outer portion of the hearing protection device;
determining that the first value exceeds the first threshold;
identifying an elapsed time that the user has been exposed to noise levels at or above the first value; and
notifying at least the second computing device, the notifying indicating the elapsed time that the user has been exposed at or above the first value.

4. The method of claim 3, further comprising transmitting, over a network and to a data store, the first value, the second value, and the elapsed time.

5. The method of claim 1, further comprising:
determining that the hearing protection device is not within a threshold signal strength range of the first computing device;
measuring, by the first computing device, the noise level of the environment, wherein the determining, by the first computing device, that the first value exceeds a first threshold occurs subsequent to the measuring; and
notifying, based on the determining that the hearing protection device is not within a threshold signal strength range and based on the measuring of the noise level, the second computing device, the notifying indicating that the user is not wearing the hearing protection device.

6. The method of claim 1, wherein the first computing device is a first mobile device of the user and the second computing device is a second mobile device of a second user.

7. The method of claim 1, wherein the first computing device is a remote server computing device and the second computing device is a mobile device of the user.

* * * * *